United States Patent
Drewry et al.

(10) Patent No.: US 7,018,379 B2
(45) Date of Patent: Mar. 28, 2006

(54) FLEXIBLE SPINAL STABILIZATION SYSTEM AND METHOD

(75) Inventors: Troy D. Drewry, Memphis, TN (US); Fred J. Molz, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/793,308

(22) Filed: Mar. 4, 2004

(65) Prior Publication Data

US 2004/0172025 A1    Sep. 2, 2004

Related U.S. Application Data

(62) Division of application No. 10/013,053, filed on Oct. 30, 2001, now Pat. No. 6,783,527.

(51) Int. Cl.
    *A61B 17/58*    (2006.01)
(52) U.S. Cl. ............................................. 606/61
(58) Field of Classification Search ............ 606/61, 606/73, 90, 105
    See application file for complete search history.

(56) References Cited

U.S. PATENT DOCUMENTS

| | | | |
|---|---|---|---|
| 4,041,939 A * | 8/1977 | Hall | 606/61 |
| 4,790,850 A | 12/1988 | Dunn et al. | |
| 4,932,972 A | 6/1990 | Dunn et al. | |
| 5,092,866 A | 3/1992 | Breard et al. | |
| 5,129,388 A | 7/1992 | Vignaud et al. | |
| 5,180,393 A | 1/1993 | Commarmond | |
| 5,181,917 A * | 1/1993 | Rogozinski | 606/61 |
| 5,261,907 A | 11/1993 | Vignaud et al. | |
| 5,261,911 A | 11/1993 | Carl | |
| 5,282,802 A | 2/1994 | Mahony, III | |
| 5,282,863 A | 2/1994 | Burton | |
| 5,312,404 A | 5/1994 | Asher et al. | |
| 5,346,493 A | 9/1994 | Stahurski et al. | |
| 5,350,380 A | 9/1994 | Goble et al. | |
| 5,364,400 A | 11/1994 | Rego, Jr. et al. | |
| 5,382,248 A | 1/1995 | Jacobson et al. | |
| 5,385,583 A | 1/1995 | Cotrel | |
| 5,387,213 A | 2/1995 | Breard et al. | |
| 5,397,356 A | 3/1995 | Goble et al. | |

(Continued)

FOREIGN PATENT DOCUMENTS

EP    0 669 109    2/1994

(Continued)

OTHER PUBLICATIONS

Dynesys™ The spinal implant for dynamic re-stabilization of spinal segments in case of intervertebral disc damage. Keeping vertebrae mobile, it ensures a better quality for life, Sulzer Technology Corporation, 7 pgs.

*Primary Examiner*—Eduardo C. Robert
*Assistant Examiner*—Annette Reimers
(74) *Attorney, Agent, or Firm*—Woodard, Emhardt Moriarty, McNett & Henry LLP

(57) ABSTRACT

Devices, methods and systems for stabilizing at least a portion of the spinal column are provided. Devices include anchors and coupling members for engaging an elongate member. Systems include an elongate member sized to span a distance between at least two vertebral bodies and being at least partially formed of a flexible material. A number of anchors and coupling members are used to secure the elongate member to each of the vertebral bodies. The anchors can be compressed towards one another and the elongate member secured thereto and/or the elongate member can be tensioned to provide corrective forces to the spine.

15 Claims, 10 Drawing Sheets

U.S. PATENT DOCUMENTS

| | | |
|---|---|---|
| 5,425,767 A | 6/1995 | Steininger et al. |
| 5,429,639 A | 7/1995 | Judet |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,562,663 A | 10/1996 | Wisnewski et al. |
| 5,630,817 A | 5/1997 | Rokegem et al. |
| 5,643,260 A | 7/1997 | Doherty |
| 5,643,266 A | 7/1997 | Li |
| 5,653,710 A | 8/1997 | Harle |
| 5,658,284 A | 8/1997 | Sebastian et al. |
| 5,697,929 A | 12/1997 | Mellinger |
| 5,782,831 A * | 7/1998 | Sherman et al. .............. 606/61 |
| RE36,221 E | 6/1999 | Breard et al. |
| 5,928,231 A | 7/1999 | Klein et al. |
| 6,004,349 A | 12/1999 | Jackson |
| 6,139,550 A * | 10/2000 | Michelson .................... 606/69 |
| 6,193,719 B1 | 2/2001 | Gournay et al. |
| 6,193,721 B1 * | 2/2001 | Michelson .................... 606/70 |
| 6,224,598 B1 * | 5/2001 | Jackson ....................... 606/61 |
| 6,530,929 B1 * | 3/2003 | Justis et al. ................. 606/103 |
| 6,616,666 B1 * | 9/2003 | Michelson .................... 606/61 |
| 6,616,667 B1 * | 9/2003 | Steiger et al. ................ 606/61 |

FOREIGN PATENT DOCUMENTS

| | | |
|---|---|---|
| WO | WO 92/20294 | 11/1992 |
| WO | WO01/28436 | 4/2001 |

* cited by examiner

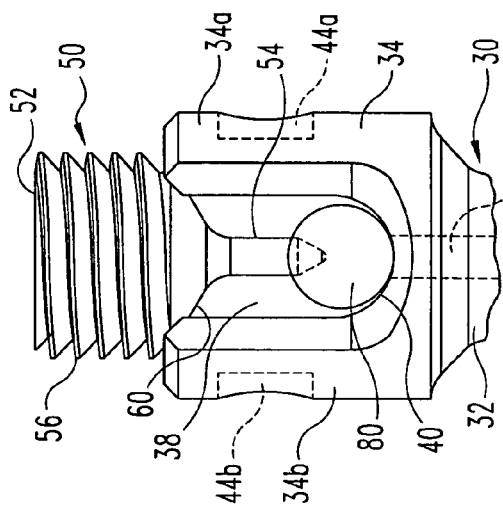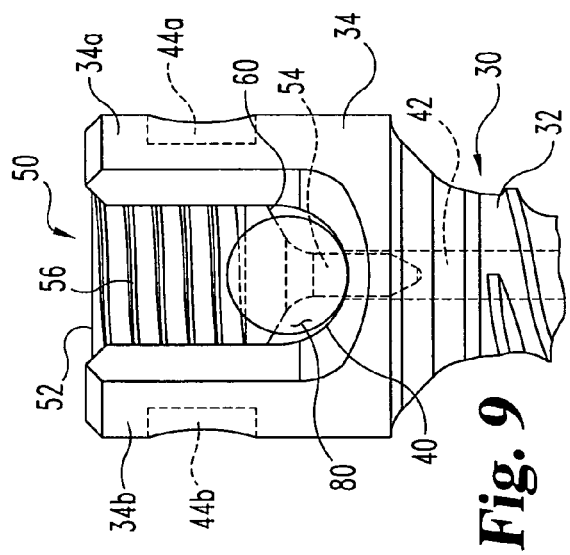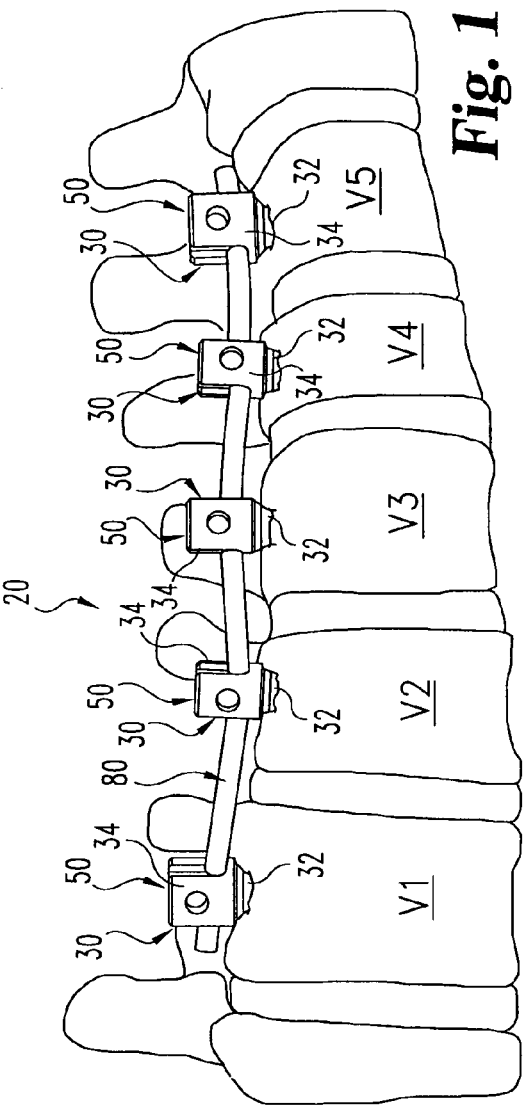

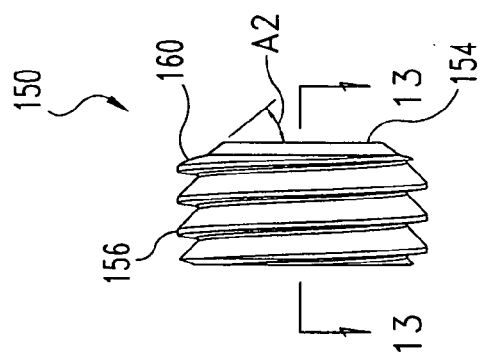
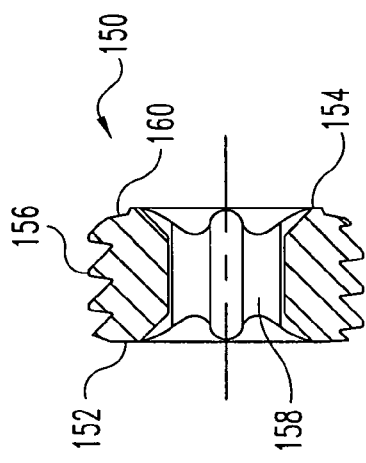
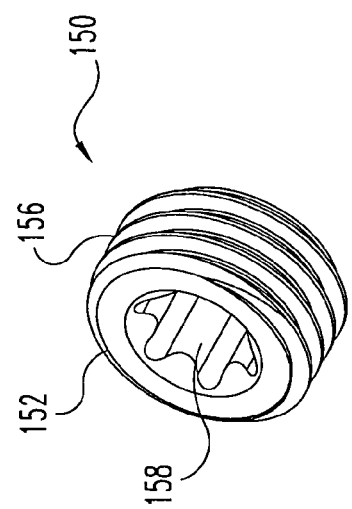
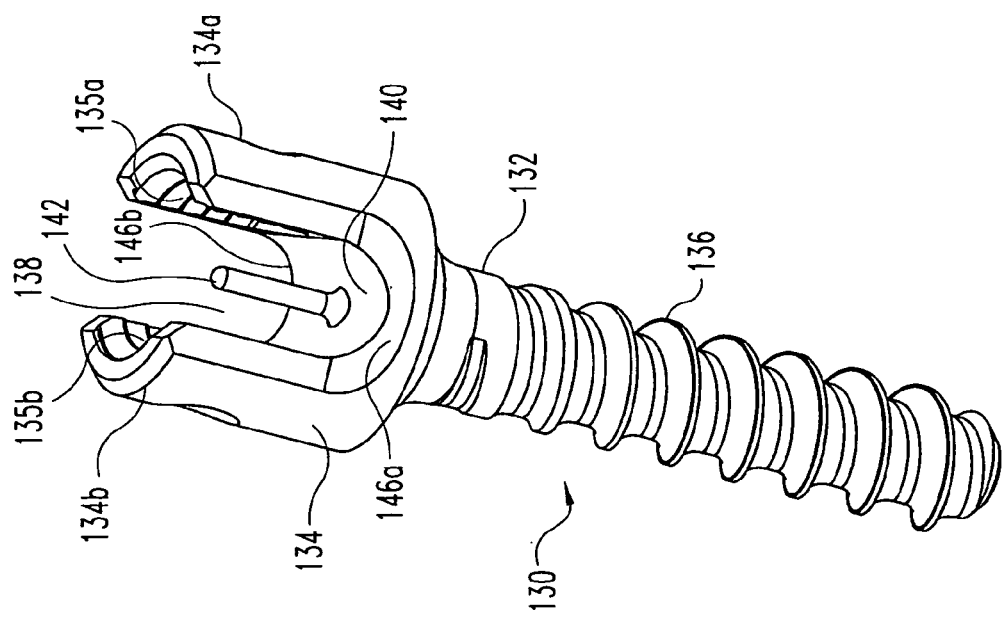

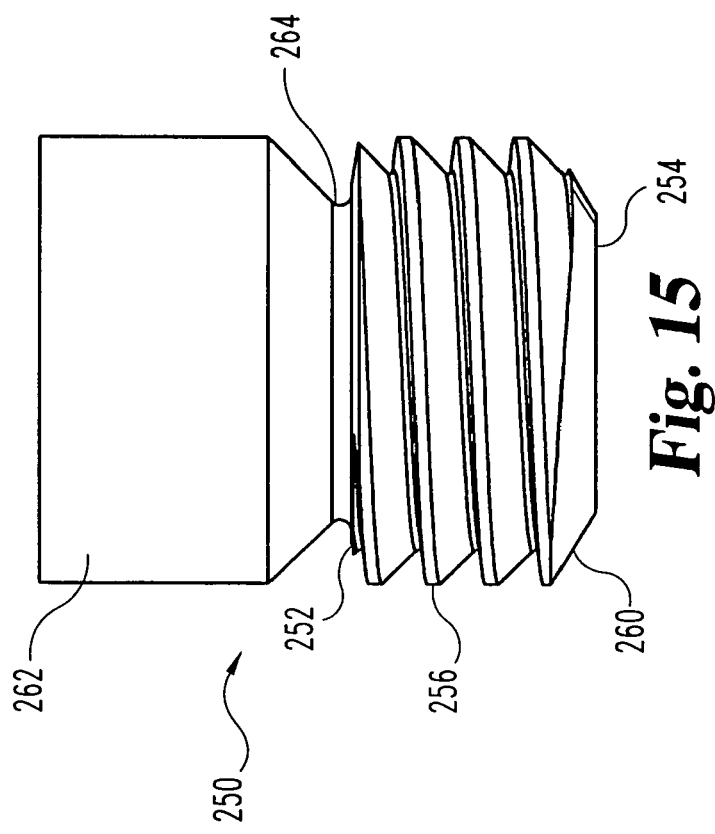
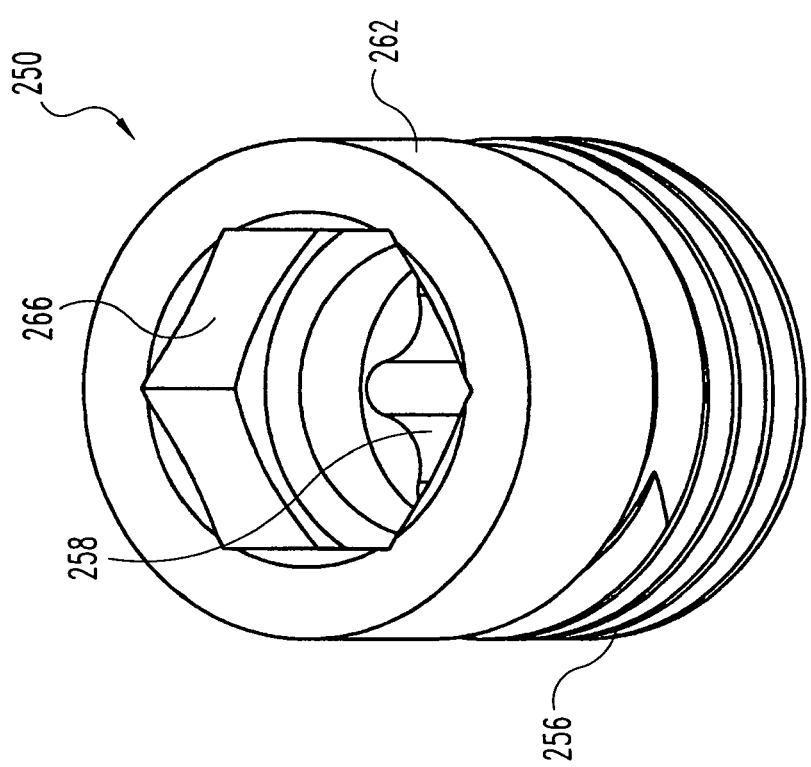

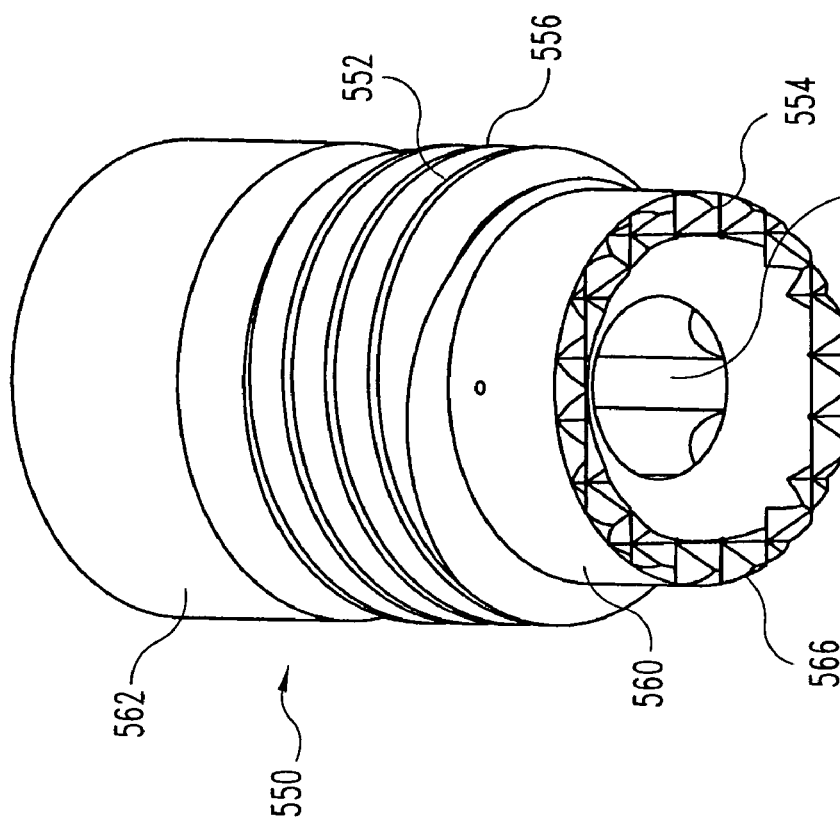
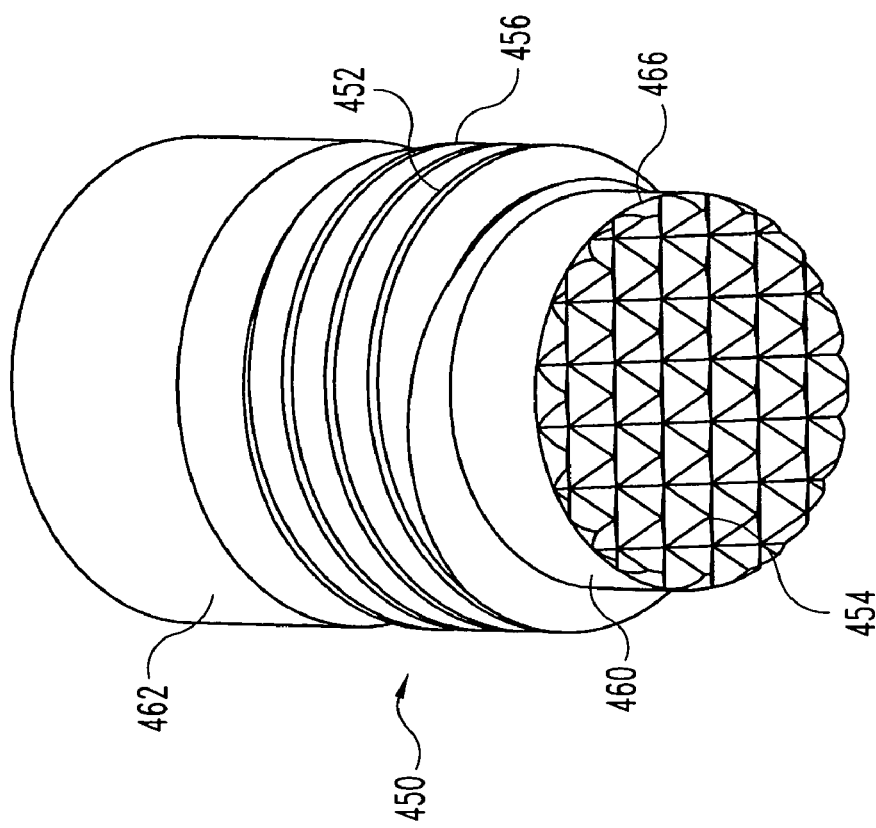

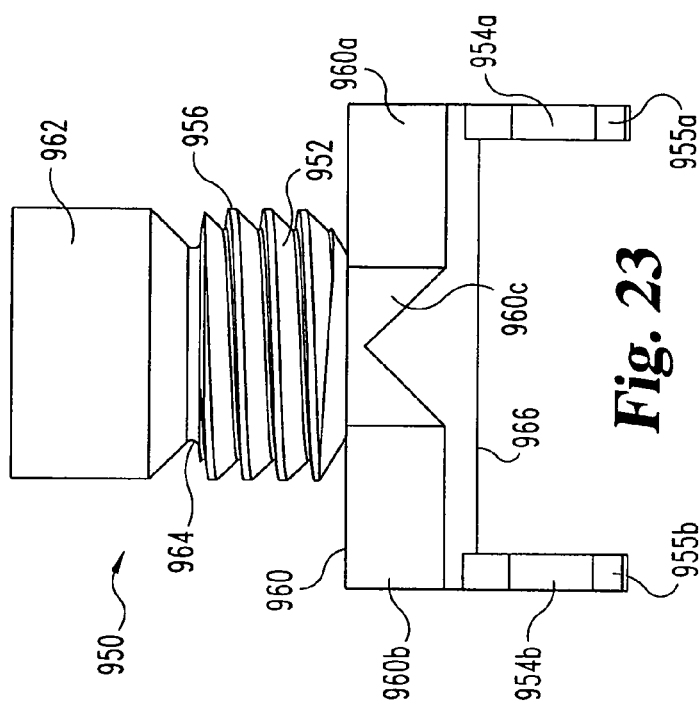
*Fig. 23*
*Fig. 23a*
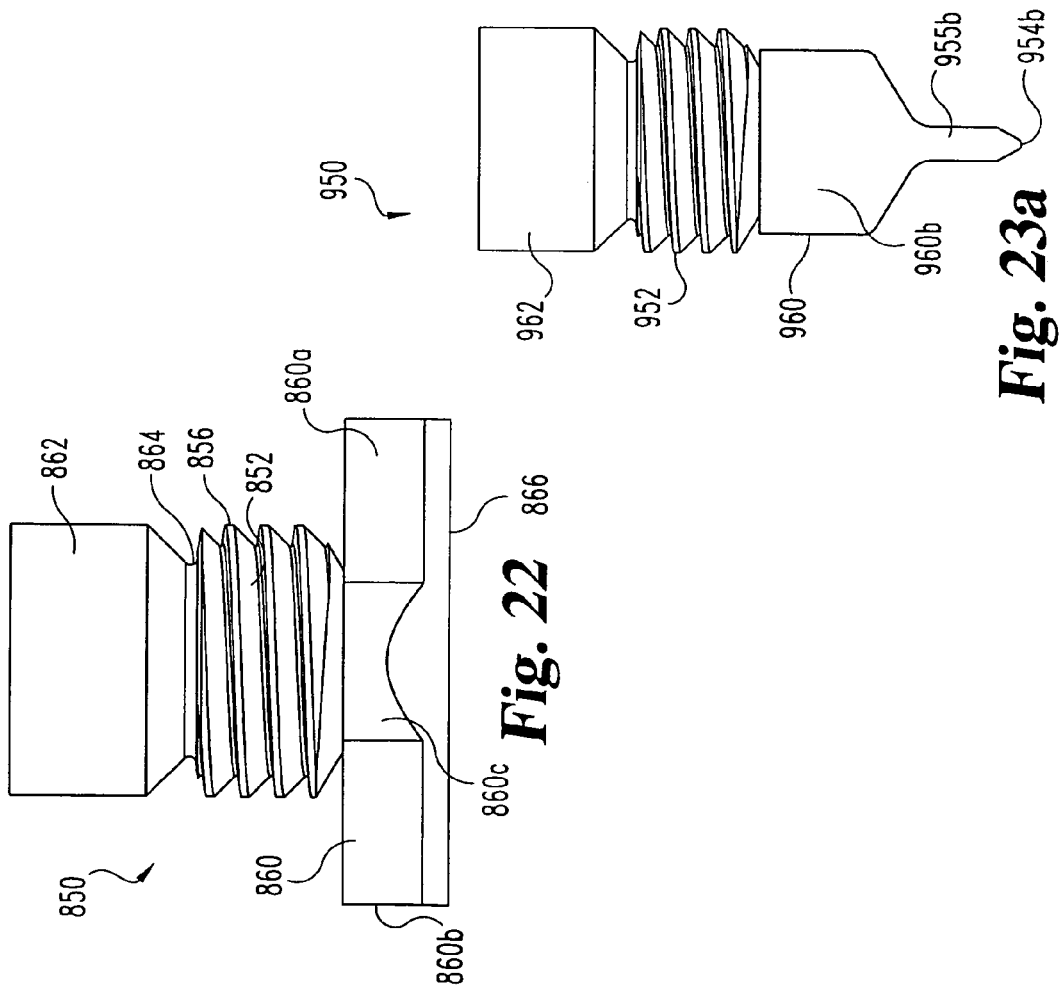
*Fig. 22*

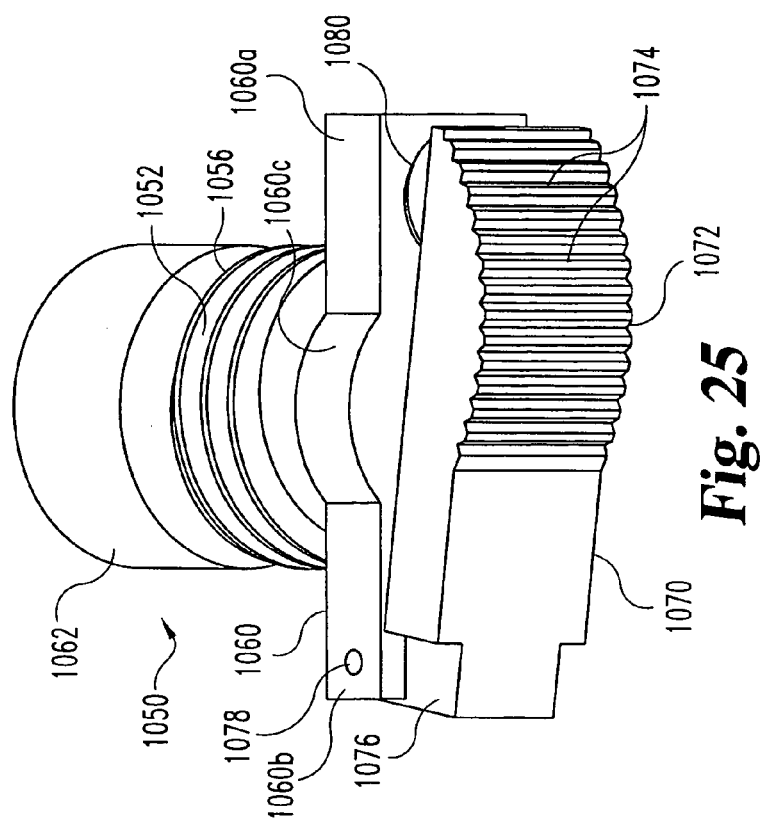
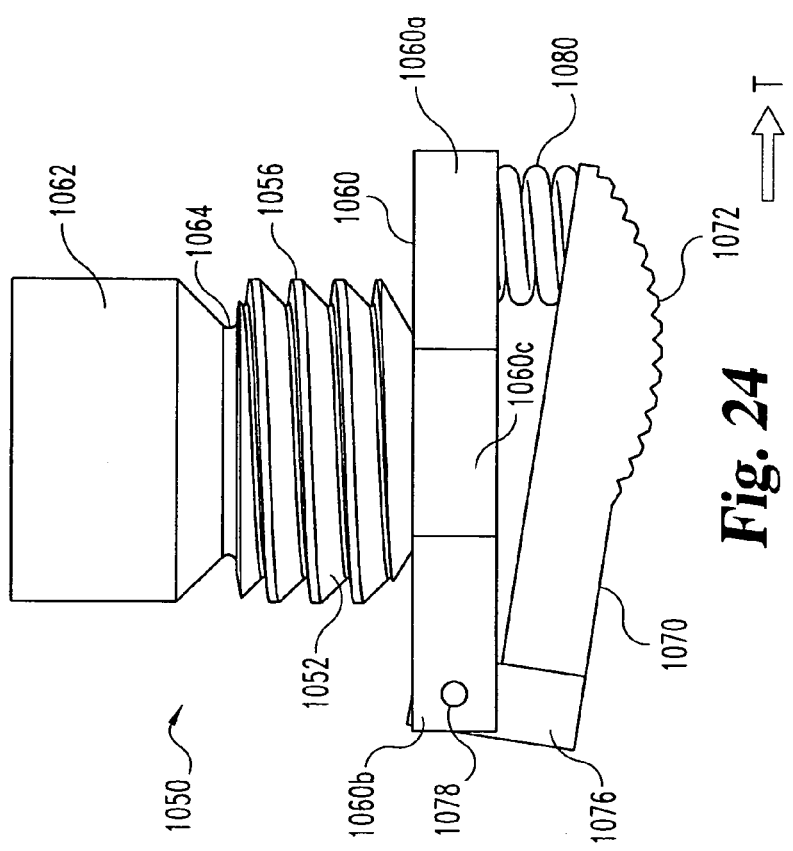

FLEXIBLE SPINAL STABILIZATION SYSTEM AND METHOD

CROSS-REFERENCE TO RELATED APPLICATION

This application is a divisional of U.S. patent application Ser. No. 10/013,053 filed on Oct. 30, 2001 now U.S. Pat. No. 6,783,527, which is hereby incoporated by reference in its entirety.

FIELD OF THE INVENTION

The present invention relates generally to the field of instrumentation, devices, and systems for treatment of the spine, and more particularly to methods and systems for interconnecting two or more portions of the spine and also devices for engaging an elongate member.

BACKGROUND OF THE INVENTION

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment.

While the external stabilization systems of the prior art are a step in the right direction, there remains room for additional improvements. Oftentimes, the geometric and dimensional features of these systems and patient anatomy constrain the surgeon during surgery and prevent optimal placement, attachment and loading of the spinal motion segment.

Thus, there is a general need in the industry to provide methods and devices for stabilizing a spinal motion segment that reduce surgeon constraints during surgery and optimize placement and attachment of the stabilization devices to the spinal motion segment. There are also needed improved devices for connecting longitudinal members to the spinal column. There is also a need for stabilization devices that allow segmental motion to be maintained after attachment thereto. There are further needs for stabilization devices that maintain the desired corrective forces on the spinal motion segment. The present invention is directed to meeting these needs and others in a novel and unobvious manner.

SUMMARY OF THE INVENTION

The present invention provides a system with anchors interconnected by a flexible elongate member. Coupling members secure the elongate member to the anchors to maintain the corrective forces applied to the spinal motion segment by the elongate member.

The present invention further provides an anchor to which an elongate member can be attached. A coupling member can be coupled to the anchor to further secure the elongate member to the anchor.

The present invention also provides a cannulated anchor which receives a portion of a coupling member in the cannulation when the coupling member is coupled to the anchor. An elongate member can also be placed between the coupling member and the anchor, with the portion of the coupling member extending through the elongate member.

The present invention also provides an anchor having a penetrating element which at least partially penetrates an elongate member. A coupling member can be secured to the anchor. In one form, the penetrating element is received in the coupling member.

The present invention additionally provides a coupling member attachable to an anchor. The coupling member can be provided with any one of a number of variously configured elongate member engaging portions that penetrate and/or crimp an elongate member positioned between the coupling member and the anchor.

Methods for engaging an elongate member to a spinal motion segment are also provided. According to one method, first and second anchors are engaged to first and second vertebrae and compressed toward one another. An elongate member is engaged to the first and second anchors. According to another method, the elongate member is tensioned before it is attached to the anchors.

Further aspects, forms, objects, features, advantages and benefits of the present invention will become apparent from the drawings and description contained herein.

BRIEF DESCRIPTION OF THE DRAWINGS

FIG. 1 is an elevational view of a spinal motion segment with a spinal fixation system according to the present invention attached thereto.

FIG. 8 is an elevational view of an elongate member positioned in the anchor of FIG. 2 with the coupling member of FIG. 4 positioned for engagement to the anchor.

FIG. 9 is an elevational view of an elongated member positioned in the anchor of FIG. 2 with the coupling member of FIG. 4 engaged to the anchor and extending through the elongate member.

FIG. 10 is a perspective view of another embodiment anchor according to the present invention.

FIG. 11 is a perspective view of another embodiment coupling member according to the present invention.

FIG. 12 is an elevational view of the coupling member of FIG. 11.

FIG. 13 is a cross-sectional view through line 13—13 of FIG. 12.

FIG. 14 is a perspective view of another embodiment coupling member according to the present invention.

FIG. 15 is an elevational view of the coupling member of FIG. 14.

FIG. 18 is a perspective view of another embodiment coupling member according to the present invention.

FIG. 19 is a perspective view of another embodiment coupling member according to the present invention.

FIG. 22 is an elevational view of another embodiment coupling member according to the present invention.

FIG. 23 is an elevational view of another embodiment coupling member according to the present invention.

FIG. 23a in an end elevational view of the coupling member of FIG. 23.

FIG. 24 is an elevational view of another embodiment coupling member according to the present invention.

FIG. 25 is a perspective view of the coupling member of FIG. 24.

DESCRIPTION OF THE ILLUSTRATED EMBODIMENTS

Figure 2:
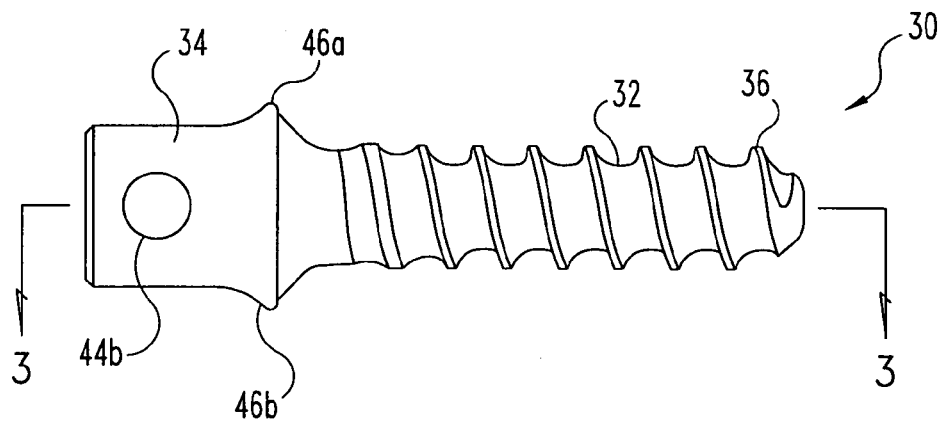
FIG. 2 is an elevational view of an anchor according to one aspect of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

FIG. 1 depicts a spinal stabilization system 20 according to one embodiment of the present invention for stabilizing at least a portion of the vertebral column. Stabilization system 20 is shown attached to a spinal motion segment that extends across a plurality of vertebrae V1, V2, V3, V4, V5. Stabilization system 20 includes an elongate member 80 secured to a plurality of anchors 30. Each anchor 30 is engaged to a respective one of the vertebrae V1, V2, V3, V4, V5. A coupling member 50 is engaged to each of the anchors 30 with elongate member 80 positioned between each anchor 30 and its respective coupling member 50.

It should be understood that system 20 may be utilized in all regions of the spine, including the cervical, thoracic, lumbar, lumbo-sacral and sacral regions of the spine. It should also be understood that system 20 may extend across a spinal motion segment having only two vertebrae or more than two vertebrae. It is further contemplated two or more stabilization systems may be employed simultaneously along the same spinal motion segment. Additionally, although system 20 is shown in FIG. 1 as having application in a posterior region of the spinal motion segment, system 20 may alternatively be applied in other surgical approaches and combinations of surgical approaches to the spinal motion segment such that one or more stabilization systems 20 are attached to the anterior, antero-lateral, lateral, and/or postero-lateral portions of the spinal motion segment.

Stabilization system 20 allows at least small degrees of spinal motion in the spinal motion segment to which it is attached since system 20 includes an elongate member 80 that is at least partially flexible between adjacent anchors 30. It should be understood that stabilization system 20 can be used in conjunction with fusion or non-fusion treatment of the spine. In one form, elongate member 80 is a tether made from one or polymers, such as, for example, polyester or polyethylene; one or more superelastic metals or alloys, such as, for example, nitinol; or from resorbable synthetic materials, such as, for example suture material or polylactic acid. It is further contemplated that elongate member 80 has elasticity such that when tensioned it will tend to return toward its pre-tensioned state.

The anchors and coupling members described herein may be employed with stabilization system 20. In addition, it contemplated that the anchors and coupling members described herein may be employed in isolation or in systems that include two or more coupling members and anchors. Examples of other systems include: one or more elongate members extending laterally across a vertebral body; one or more elongate members extending in the anterior-posterior directions across a vertebral body; one or more elongate member wrapped around a vertebral body; and combinations thereof. Further examples include application of the anchors and coupling members of the present invention with bony structures in regions other than the spinal column.

Figure 3:
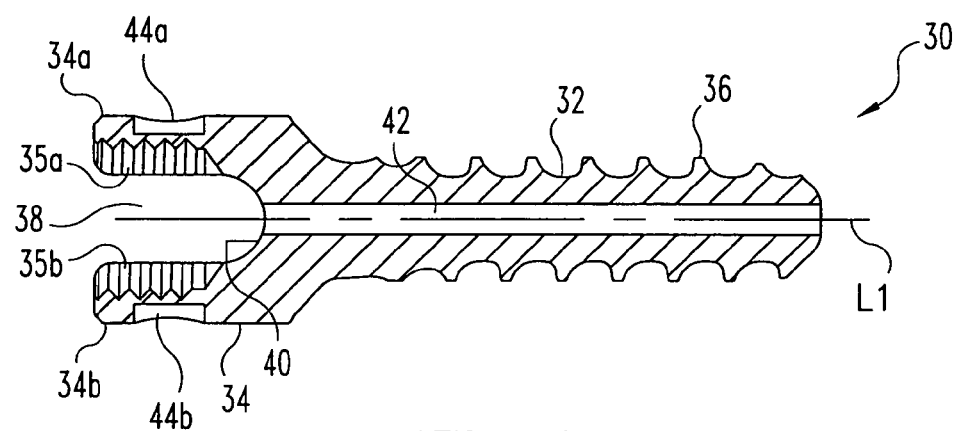
FIG. 3 is a cross-sectional view through line 3—3 of FIG. 2.
Figure 4:
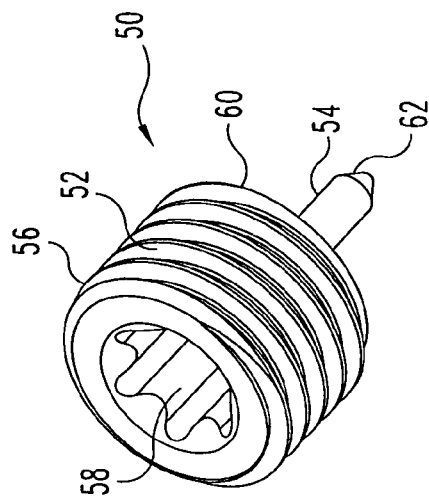
FIG. 4 is a perspective view of a coupling member according to another aspect of the present invention.
Figure 7:
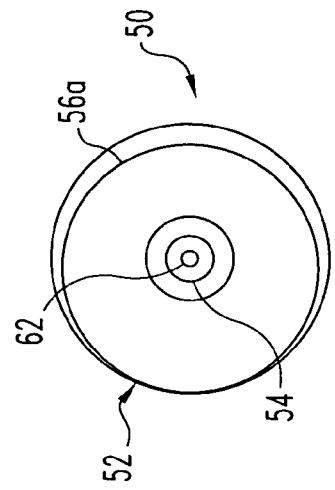
FIG. 7 is an end view of the coupling member of FIG. 4.
Figure 6:
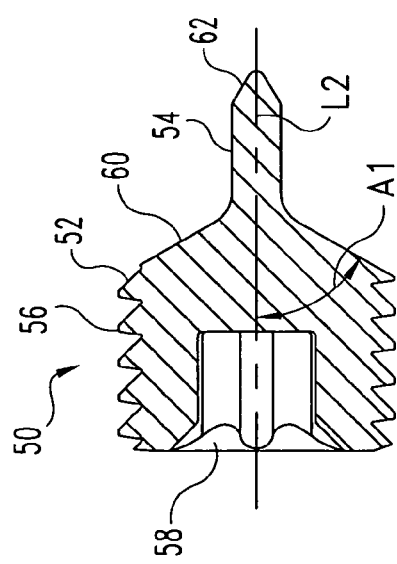
FIG. 6 is a cross-sectional view through line 6—6 of FIG. 5.
Figure 5:
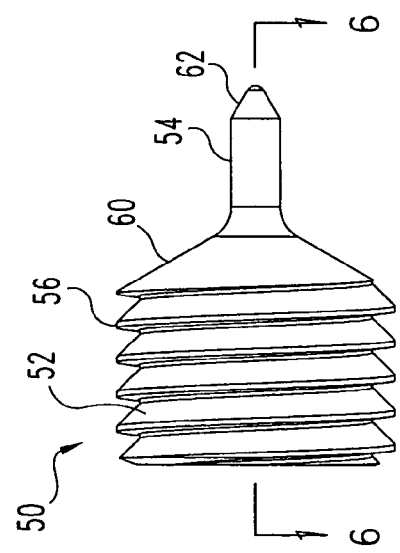
FIG. 5 is an elevational view of the coupling member of FIG. 4.

Referring to FIGS. 2–3, shown therein are various details of an anchor 30 according to the present invention. Anchor 30 has a length extending along longitudinal axis L1 and includes an elongated shaft 32 and an elongate member receiving portion in the form of a head 34. Shaft 32 can include an external thread form 36 in the form of a single thread turn or a plurality of discrete threads. Other engaging structure along shaft 32 are also contemplated, such as barbs or pivoting gulls, so long as shaft 32 can engage the bony tissue of the vertebra to which anchor 30 is attached. In an alternate form, shaft 32 is in the form of a spinal hook.

In the illustrated embodiment, head 34 has a first arm 34a spaced from a second arm 34b. Head 34 defines a U-shaped passage 38 extending between first arm 34a and second arm 34b. Head 34 further includes a bearing surface 40 extending between first arm 34a and second arm 34b and along passage 38. Bearing surface 40 further extends from a first lip 46a at one end passage 38 to a second lip 46b at the other end of passage 38. Anchor 30 further includes a cannulation 42 extending through shaft 32 along axis L1 and opening at the distal end of shaft 32. Cannulation 42 interrupts bearing surface 40 and is in communication with passage 38. It is also contemplated that cannulation 42 extends from bearing surface 40 into shaft 32 for only a portion of the length of shaft 32.

First arm 34a has thread form 35a on an inner side thereof and second arm 34b has a thread form 35b on an inner side thereof. First arm 34a includes a first indent 44a in an outer surface thereof and second arm 34b includes a second indent 44b in an outer surface thereof. Indents 44a, 44b are sized to receive fingers from insertion tools, compression instruments, and instruments for inserting and tensioning elongate member 80 or the like to enable their attachment to anchor 30 when anchor 30 is engaged to a vertebra.

Referring now to FIGS. 4–7, there will be described coupling member 50. Coupling member 50 has a plug body 52 with an elongate member engaging portion in the form of penetrating element 54 extending distally from plug body 52. A thread form 56 is formed around plug body 52. Thread form 56 has a thread run-out 56a on bearing surface 60. Plug body 52 further includes a tool receptacle 58 formed therein into which a driving tool is received to apply a rotary driving force to coupling member 50 to engage coupling member 50 to thread forms 35a, 35b of anchor 30. Coupling member 50 includes a lower bearing surface 60 which bears against elongate member 80 positioned between anchor 30 and coupling member 50. Penetrating element 54 includes a distal end 62 tapered to facilitate penetration of penetrating element 54 into elongate member 80.

The anchors and coupling members of the present invention can be formed from any suitable biocompatible material. Such material includes metals such as, for example, stainless steel or titanium; polymers such as, for example, polyester and polyethylene; superelastic metals or alloys such as, for example, nitinol; and resorbable synthetic materials such as, for example, suture material and polylactic acid.

Referring now to FIGS. 8–9, attachment of elongate member 80 to anchor 30 with coupling member 50 will be further described. In FIG. 8, elongate member 80 has been positioned through passage 38 and against or adjacent bearing surface 40 of anchor 30. Coupling member 50 is aligned with the upper opening between first arm 34a and second arm 34b. Distal end 62 of penetrating element 54 contacts or partially penetrates elongate member 80. In FIG. 9, coupling member 50 is threadingly advanced into head 34 until bearing surface 60 contacts elongate member 80 and crimps elongate member 80 between bearing surface 40 and bearing surface 60, and penetrating element extends completely through elongate member 80.

Where elongate member 80 is made from compressible material, elongate member 80 has a reduced cross-sectional area along its crimped portion between bearing surfaces 40, 60. Penetrating element 54 is at least partially received in cannulation 42 of anchor 30, allowing complete penetration of elongate member 80 by penetrating element 54 in combination with the crimping discussed above. Penetrating element 54 provides a bearing member against which elongate member 80 acts as its is tensioned or compressed with longitudinal forces that would tend to cause elongate member 80 slip in anchor 30. Movement of elongate member 80 in anchor 50 is thus resisted by friction generated between elongate member 80 and bearing surfaces 40, 60 and also by the bearing support provided by the penetrating element 54 of coupling member 50.

In FIG. 10, there is illustrated another embodiment anchor 130 according to the present invention. Anchor 130 includes an elongated shaft 132 and a head 134. Shaft 132 can include external thread form 136 or other bone engaging structure therealong such as discussed above with respect to anchor 30. In the illustrated embodiment, head 134 as ab elongate member receiving portion between a first arm 134a spaced from a second arm 134b. First arm 134a has thread form 135a on an inner side thereof and second arm 134b has a thread form 135b on an inner side thereof. Head 134 defines a U-shaped passage 138 extending between first arm 134a and second arm 134b. Head 134 further includes a bearing surface 140 extending between first arm 134a and second arm 134b and along passage 138 to a first lip 146a to a second lip 146b.

Anchor 130 further includes an elongate member engaging portion in the form of a penetrating element 142 extending from bearing surface 140 into passage 138. Elongate member 80 can be placed into passage 138 and pressed against bearing surface 140 such that penetrating element 142 extends through elongate member 80. Penetrating element 142 provides a bearing member against which elongate member 80 acts to resist tensile or compressive longitudinal forces that would tend to cause elongate member 80 slip in anchor 130. It is further contemplated in another embodiment that anchor 130 is not provided with penetrating element 142.

Referring now to FIGS. 11-13, another embodiment coupling member 150 according to the present invention and having application with anchors 30, 130 is illustrated. Coupling member 150 has a plug body 152 with a thread form 156 therearound. Coupling member 150 includes a distal bearing surface 160 which bears against elongate member 80 when positioned between anchor 30, 130 and coupling member 150. Coupling member 150 also includes an elongate member engaging portion on its distal end in the form of a protrusion 154 extending around a tool receptacle 158. Tool receptacle 158 provides a through-hole by extending through plug body 152. A driving tool is positionable in tool receptacle 158 to apply a rotary driving force to coupling member 150 to engage coupling member 150 to the internally threaded head of anchor 30, 130.

Coupling member 150 presses elongate body 80 between bearing surface 160 and the bearing surface in the passage of anchor 30, 130. Protrusion 154 crimps elongate member 80 at its contact locations therewith against the bearing surface of the anchor to a reduced size configuration to resist longitudinal forces exerted on the elongated member. Coupling member 150 crimps elongate member 80 at a first location adjacent first lip 46a, 146a of anchor 30, 130 and at a second location adjacent second lip 46b, 146b of anchor 30, 130. For embodiments in which penetrating element 142 is provided on anchor 130, penetrating element 142 extends through elongate member 80 and into receptacle 158 of coupling member 150 when threadingly engaged to anchor 130. Penetrating element 142 provides resistance to longitudinal forces applied to elongate member 80 in manner similar to that discussed above with respect to penetrating element 54.

Referring now to FIGS. 14–15, a coupling member 250 according to the present invention and having application with anchors 30, 130 is illustrated. Coupling member 250 has a plug body 252 with a thread form 256 therearound. Coupling member 250 includes a distal bearing surface 260 which bears against elongate member 80 positioned between anchor 30, 130 and coupling member 250. Coupling member 250 also includes an elongate member engaging portion in the form of a protrusion 254 extending around a tool receptacle 258. Tool receptacle 258 extends through plug body 252. A driving tool is positionable in tool receptacle 258 to apply a rotary driving force to coupling member 250 to engage coupling member 250 to the internally threaded head of anchor 30, 130.

Coupling member 250 further includes a break-off portion 262 coupled to plug body 252 at recess 264. Break-off portion 262 has a driving tool receiving portion 266 formed around tool receptacle 258. In the illustrated embodiment, driving tool receiving portion 266 is configured to receive a hex-head driving tool; however, other configurations are also contemplated. A driving tool is positionable in driving tool receiving portion 266 to drive coupling member 250 into the head of anchor 30, 130 so that protrusion 254 crimps elongate member 80 at its contact locations therewith against the bearing surface of the anchor to resist longitudinal forces exerted thereon. It is also contemplated protrusion 254 can partially penetrate into elongate member 80 at its contact locations therewith. Break-off portion 262 severs from plug body 252 at recess 264 when a pre-determined amount of torque is applied thereto. The torque is established such that sufficient compressive forces are applied to elongate member 80 to prevent it from slipping with respect to anchor 30, 130, yet the compressive forces are not so great so as to sever or otherwise cause elongate member 80 to be ineffective as a stabilization element.

For embodiments in which penetrating element 142 is provided on anchor 130, penetrating element 142 extends through elongate member 80 and into the through-hole provided by receptacle 258 of coupling member 250 when threadingly engaged to anchor 130. Break-off portion 262 is sized positioned with respect to plug body 252 so that the driving tool is located proximally of tool receptacle 258 and does not interfere with penetrating element 142 as coupling member 250 is threaded into head 134 of anchor 130.

Figure 17:
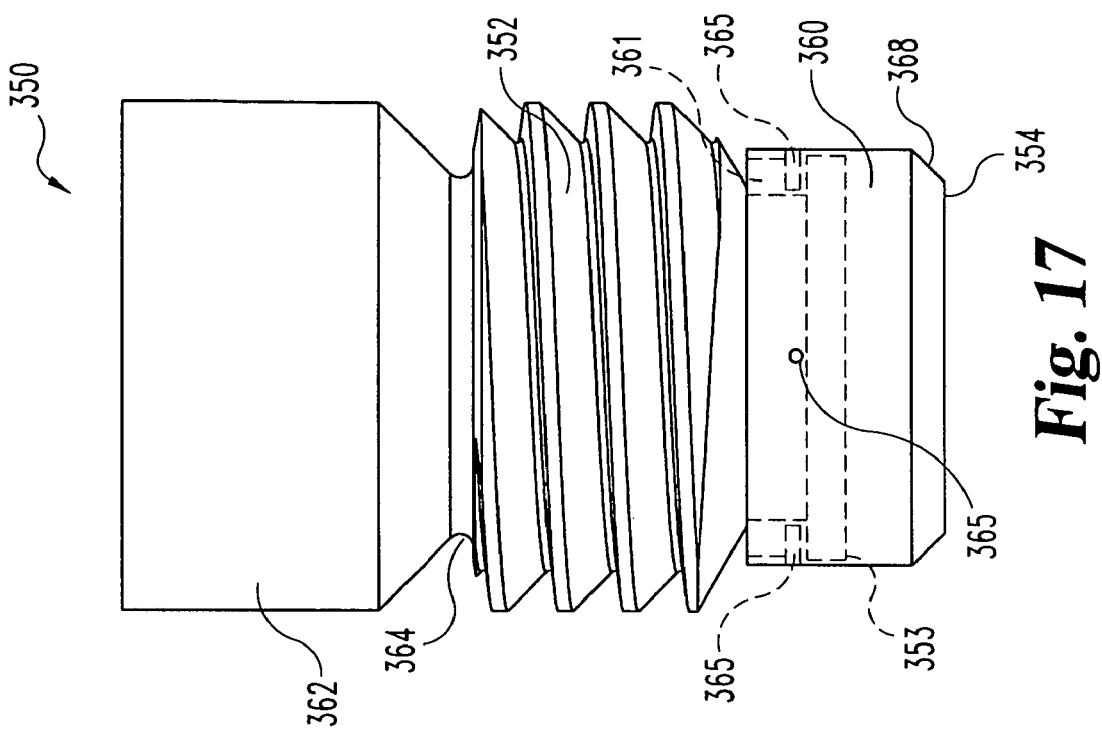
FIG. 17 is an elevational view of the coupling member of FIG. 16.
Figure 16:
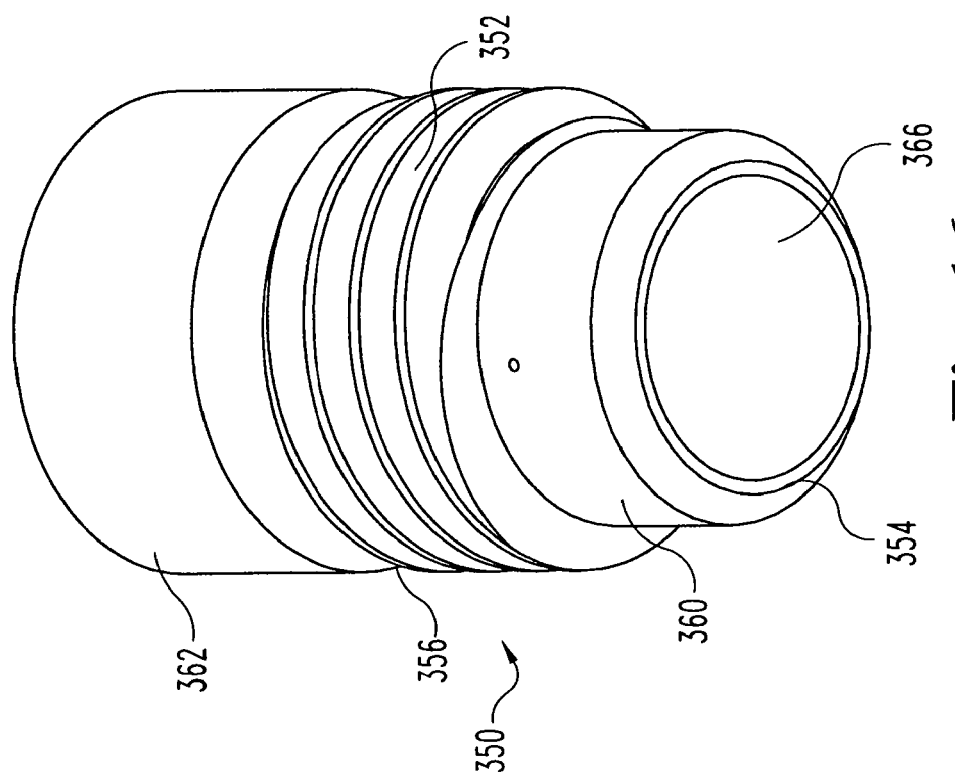
FIG. 16 is a perspective view of another embodiment coupling member according to the present invention.

Referring now to FIGS. 16–17, a coupling member 350 according to the present invention and having application with anchors 30, 130 is illustrated. Coupling member 350 has a plug body 352 with a thread form 356 therearound. Coupling member 350 also includes an elongate member engaging portion in the form of a cylindrical end member 360 that is attached to a distal end of plug body 352. End member 360 is rotatable relative to plug body 352 such that as plug body 352 is threaded into the head of the anchor, end member 360 does not rotate when in sufficiently firm contact with elongate member 80. In specific embodiment, plug body 352 includes a lower flange 353 received in an upper cavity 361 of end member 360. A number of pine 365 are press fit or otherwise attached to end member 360 and extend into cavity 361 above flange 353 to rotatably capture end member 360 on plug body 352. Other configurations for rotatably engaging end member 360 to plug body 352 are also contemplated herein.

End member 360 includes a lower bearing surface 368 which bears against elongate member 80 when elongate member 80 is positioned between anchor 30, 130 and coupling member 350. End member 360 also includes a protrusion 354 extending around a concave surface 366. Protrusion 354 crimps or partially penetrates elongate member 80 at its contact points therewith against the anchor bearing surface.

Coupling member 350 includes a tool receptacle (not shown) that at least extends through plug body 352. The tool receptacle may extend through end member 360 to receive a penetrating element extending from the anchor. It is further contemplated that concave surface 366 can be solid and contact the anchor penetrating element when coupling member 350 is engaged thereto, or that the penetrating element only partially penetrates the elongate member. Coupling member 350 can also include a break-off portion 362 and recess 364 such as described above with respect to coupling member 250.

Referring now to FIG. 18, a coupling member 450 according to the present invention and having application with anchors 30, 130 is illustrated. Coupling member 450 has a plug body 452 having a thread form 456 therearound. Coupling member 450 also includes an elongate member engaging portion in the form of cylindrical end member 460 that is attached to plug body 452 and rotatable with respect thereto. Coupling member 450 includes a tool receptacle (not shown) that extends through plug body 452 but not through end member 460. Coupling member 450 can also include a break-off portion 462 such as described above with respect to coupling member 250. End member 460 includes a lower bearing surface 466 having protrusions 454 which partially penetrate or crimp elongate member 80 against the anchor bearing surface at a number of locations between first lip 46a, 146a and second lip 46b, 146b. In the illustrated embodiment, these irregularities are formed by a grid of a plurality of pyramid shaped protrusions.

An alternate form of coupling member 450 is shown in FIG. 19 and designated at 550. Coupling member 550 is generally identical to coupling member 450 and includes a plug body 552 having a thread form 556 therearound, a break-off portion 562, and a cylindrical end member 560 having a lower bearing surface 566 with protrusions 554 that are similar to protrusions 454. Coupling member 550 further includes passage 558 extending therethrough and opening at lower bearing surface 566. While coupling member 550 may be used with any embodiment anchor discussed herein, coupling member 550 is particularly useful if anchor 130 is provided with a penetrating element 142 since penetrating element 142 can completely penetrate the elongate member and be received in passage 558.

Figure 21:
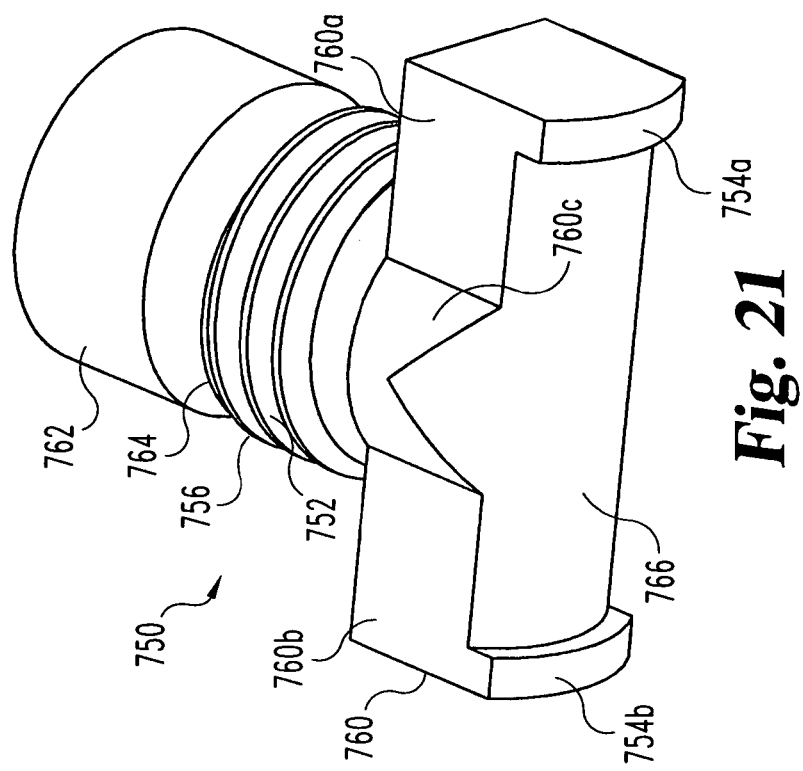
FIG. 21 is another perspective view of the coupling member of FIG. 20.
Figure 20:
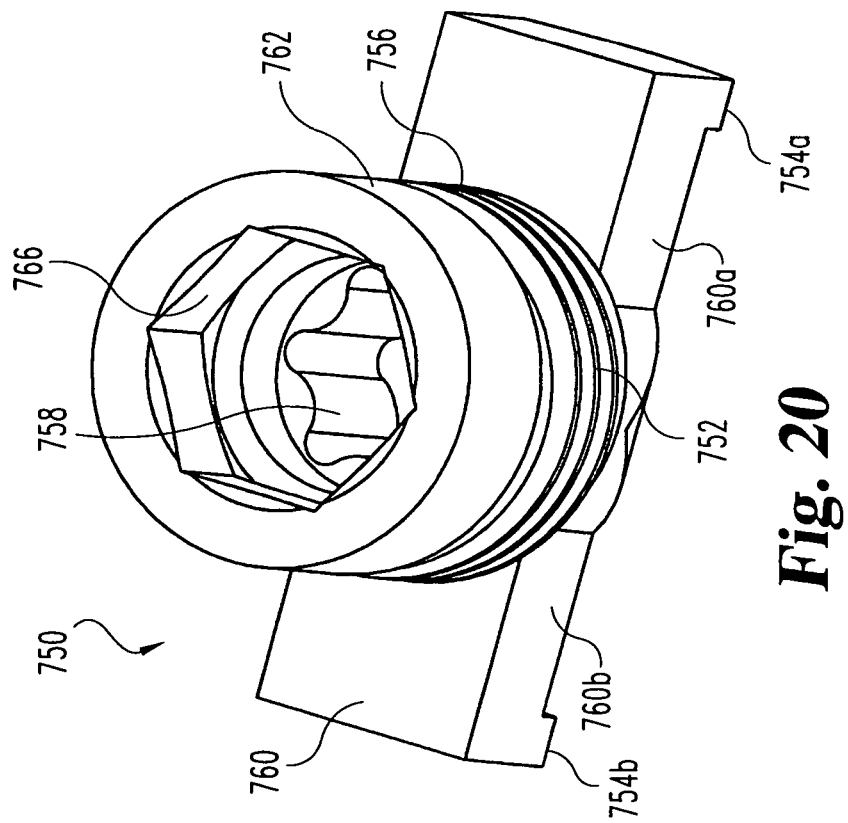
FIG. 20 is a perspective view of another embodiment coupling member according to the present invention.

Referring now to FIGS. 20–21, another embodiment coupling member 750 is illustrated. Coupling member 750 has a plug body 752 having a thread form 756 therearound. Coupling member 750 includes a tool receptacle (not shown) that extends at least through plug body 752. Coupling member 750 can also include a break-off portion 762 such as described above with respect to coupling member 250. Coupling member 750 includes elongate member engaging portion having an end member 760 on rotatably engage to plug body 752.

End member 760 is an elongated body having a first longitudinal extension 760a and a second longitudinal extension 760b extending from a center portion 760c. Center portion 760c is sized and shaped to be received in the passage of the anchor adjacent the anchor bearing surface. Longitudinal extensions 760a, 760b are sized to be received in passage 38, 138 of anchor 30, 130 and extending longitudinally in the direction of elongate member 80 between the anchor arms and beyond the adjacent one of the first lip 46a, 146a and second lip 46b, 146b. A lower bearing surface 766 is formed along end member 760 between a first protrusion 754a and a second protrusion 754b. Protrusions 754a, 754b contact elongate member 80 and crimp it between lip 46a, 146a or 46b, 146b and the adjacent protrusion 754a, 754b. Lower bearing surface 766 contacts elongate member 80 in the passage of the anchor such that a frictional bearing relationship is established between lower bearing surface 766 and the entire length of the bearing surface of the anchor between lips 46a, 46b or 146a, 146b.

An alternate form of coupling member 750 is shown in FIG. 22 and designated at 850. Coupling member 850 is generally identical to coupling member 750 and includes a plug body 852 having a thread form 856 therearound, a break-off portion 862 and recess 864, and an end member 860 having a first longitudinal extension 860a, a second longitudinal extension 860b, a central portion 860c, and a lower bearing surface 866 extending therealong. The engagement of elongate member 80 between anchor 30, 130 and coupling member 850 relies entirely on the frictional engagement provided by the contact surface area of lower bearing surface 866 and the bearing surface of the anchor between first lip 46a, 146 and second lip 46b, 146b. Utilizing the entire length of the anchor bearing surface to crimp elongate member 80 provides greater resistance to slippage of elongate member 80 between coupling member 50 and anchor 30 than would be provided if only a portion of the bearing surface of the anchor were utilized.

Another form of coupling member 750 is shown in FIG. 23 and designated at 950. Coupling member 950 is generally identical to coupling member 750 and includes a plug body 952 having a thread form 956 therearound, a break-off portion 962 and recess 964, and an end member 960 having a first longitudinal extension 960a, a second longitudinal extension 960b, and a central portion 960c therebetween with a lower bearing surface 966 extending therealong. Coupling member 950 also includes longitudinal member engaging portions in the form of a first penetrating element 954*a* and second penetrating element 954*b* having tapered ends 955*a* and 955*b*, respectively. As shown further in FIG. 23*a*, penetrating elements 954*a*, 954*b* extend downwardly from bearing surface 966 a sufficient distance in order to partially or completely penetrate elongate member 80 positioned between anchor 30, 130 and coupling member 950. Longitudinal extensions 960*a*, 960*b* are sized to extend longitudinally along elongate member 80 beyond the passage of the anchor 30, 130 to which it is attached so that penetrating elements 954*a*, 954*b* penetrate elongate member 80 outside passage 38, 138.

Referring now to FIGS. 24–25, another embodiment coupling member 1050 is illustrated. Coupling member 1050 has a plug body 1052 having a thread form 1056 therearound. Coupling member 1050 includes a tool receptacle (not shown) that extends at least through plug body 1052. Coupling member 1050 can also include a break-off portion 1062 such as described above with respect to coupling member 250. Coupling member 1050 also includes end member 1060 in the form of an elongate body that is attached to plug body 1052 and rotatable with respect thereto.

End member 1060 includes a first longitudinal extension 1060*a*, a second longitudinal extension 1060*b*, and central portion 1060*c* therebetween. A spring loaded arm 170 is pivotally coupled at one end to second longitudinal extension 1060*b*. A spring 180 biases the opposite end of arm 1070 away from end member 1060. Arm 1070 can also include a rounded portion 1072 having protrusions in the form of a plurality of teeth 1074 formed thereacross along a lower side thereof. Elongate member 80 can be pulled or tensioned in the direction of arrow T since spring 1080 compresses to allow such tensioning. If elongate member 80 moves in the direction opposite arrow T, arm 170 provisionally captures elongate member 80 in its tensioned state with teeth 1074 spring biased against the tensioned elongate member 80. Teeth 1074 on arm 1070 frictionally engage or partially penetrate the tensioned elongate member 80 to prevent it from slipping until coupling member 1050 is secured to the anchor with spring 1080 compressed.

It is contemplated that the penetrating elements and protrusions of the present invention can extend completely through elongate member 80, or extend partially through elongate member 80. In one specific embodiment, it is contemplated that the partial penetration depth into elongate member 80 corresponds to about 5 percent of its thickness. Other penetration depths ranging from 5 percent to 100 percent are also contemplated. It is further contemplated that elongate member 80 can be provided with a substantially solid body and the penetrating elements and protrusions of the present invention pierce this solid body as coupling member is threadingly advanced into head 34.

In view of the systems and devices discussed above, a method for stabilizing a spinal motion segment will be described. An elongate member is provided with a length sufficient to extend along the spinal motion segment to which it is to be attached. Anchors are engaged to respective ones of the vertebrae comprising the spinal motion segment. Adjacent anchor can be compressed toward one another, and the elongate member attached to each of the compressed anchors to provide corrective forces to the spinal motion segment. It is contemplated that the elongate member can be crimped or penetrated as discussed above to prevent slippage of the elongate member with respect to the anchors to which it is attached. Since elongate member 80 can be penetrated or crimped at any location along its length with the anchors and coupling members of the present invention, elongate member 80 can be provided with a solid, uniform body along its length. Elongate member 80 need not include any holes, slots or other engaging features along its length for engagement to the anchors and coupling members of the present invention. Thus, the surgeon is not constrained to particular, discrete attachment locations along elongate member 80, but rather is provided an infinite number of attachment locations along elongate member 80.

According to a further method for stabilizing a spinal motion segment, an elongate member is provided with a length extending between at least two vertebrae of the spinal motion segment. Anchors are engaged to vertebrae of the spinal motion segment. The elongate member is tensioned to provide the desired corrective force to the spinal motion segment and then attached to the anchors with coupling members. It is contemplated that the elongate member can be crimped or penetrated as discussed above to prevent slippage of the elongate member with respect to the anchors to which it is attached. It is further contemplated that the first and second anchors can be compressed toward one another before the tensioned elongate member is attached to the first and second anchors. The elongate member can then be cut by the surgeon to remove any excess length.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for stabilizing a spinal motion segment, comprising:
    providing an elongate member having a length extending between at least two vertebrae and being at least partially formed of a flexible material;
    engaging a first anchor and a second anchor to respective ones of a first vertebra and a second vertebra;
    compressing the first and second anchors toward one another; and
    attaching the elongate member to each of the compressed first and second anchors so that the elongate member is crimped at least at first and second locations with respect to each of said first and second anchors.

2. The method of claim 1, further comprising:
    engaging a third anchor to a third vertebral body adjacent the second vertebral body;
    compressing the third anchor towards the second anchor; and
    attaching the elongate member to the third anchor.

3. The method of claim 1, further comprising completely penetrating the elongate member to attach it to the first and second anchors.

4. A method for stabilizing a spinal motion segment, comprising:
    providing an elongate member having a length extending between at least two vertebrae and being at least partially formed of a flexible material;
    engaging a first anchor and a second anchor to respective ones of a first vertebra and a second vertebra;
    compressing the first and second anchors toward one another;
    attaching the elongate member to each of the compressed first and second anchors so that the elongate member is crimped at least at first and second locations with respect to each of said first and second anchors; and tensioning the elongate member before attaching the elongate member to the first and second anchors.

5. The method of claim 4, wherein attaching the elongate member includes penetrating the elongate member.

6. The method of claim 5, wherein penetrating the elongate member includes piercing a solid body portion of the elongate member.

7. A method for stabilizing a spinal motion segment, comprising:
providing an elongate member having a length extending between at least two vertebrae and being at least partially formed of a flexible material;
engaging a first anchor and a second anchor to respective ones of a first vertebra and a second vertebra;
tensioning the elongate member;
penetrating the tensioned elongate member to attach the tensioned elongate member to the first and second anchors; and
compressing the first and second anchors secured to the first and second vertebrae toward one another before attaching the tensioned elongate member to the first and second anchors.

8. The method of claim 7, wherein penetrating the tensioned elongate member includes deforming the elongate member to attach the elongate member to the first and second anchors.

9. A method for stabilizing a spinal motion segment, comprising:
providing an elongate member having a length extending between at least two vertebrae and being at least partially formed of a flexible material;
engaging a first anchor and a second anchor to respective ones of a first vertebra and a second vertebra;
penetrating the elongate member to attach the elongate member to the first and second anchors;
tensioning the elongate member before penetrating the elongate member; and before attaching the elongate member to the first and second anchors.

10. The method of claim 9, wherein penetrating the elongate member includes piercing the elongate member.

11. The method of claim 9, wherein:
the first and second anchors each include an upper U-shaped channel configured for receipt of a portion of the elongate member;
the first and second anchors each include a plug with a penetrating member, the plug being movable in the channel; and
penetrating the elongate member is performed by the penetrating member of the plug.

12. A method for stabilizing a spinal motion segment, comprising:
providing an elongate member having a length extending between at least two vertebrae and being at least partially formed of a flexible material;
engaging a first anchor and a second anchor to respective ones of a first vertebra and a second vertebra;
penetrating the elongate member to attach the elongate member to the first and second anchors; and
compressing the first and second anchors secured to the first and second vertebrae toward one another before penetrating the elongate member.

13. The method of claim 12, further comprising:
engaging a third anchor to a third vertebral body adjacent the second vertebral body;
tensioning the elongate member between the second anchor and the third anchor; and
attaching the elongate member to the third anchor.

14. The method of claim 13, wherein attaching the elongate member to the third anchor includes penetrating the elongate member.

15. The method of claim 12, wherein:
the first and second anchors each include an upper U-shaped channel configured for receipt of a portion of the elongate member;
the first and second anchors each include a plug with a penetrating member, the plug being movable in the channel; and
penetrating the elongate member is performed by the penetrating member of the plug.

* * * * *